(12) United States Patent
Takahashi et al.

(10) Patent No.: US 7,696,332 B2
(45) Date of Patent: Apr. 13, 2010

(54) REPLICATION VECTOR SHOWING CELL-SPECIFIC EXPRESSION

(75) Inventors: Katsuhito Takahashi, Ikeda (JP);
Hisako Yamamura, Ikoma (JP);
Shin-ichi Miyatake, Otsu (JP)

(73) Assignee: Japan Science and Technology Agency, Kawaguchi (JP)

( * ) Notice: Subject to any disclaimer, the term of this patent is extended or adjusted under 35 U.S.C. 154(b) by 282 days.

(21) Appl. No.: 10/477,797

(22) PCT Filed: Apr. 30, 2002

(86) PCT No.: PCT/JP02/04334

§ 371 (c)(1),
(2), (4) Date: Apr. 22, 2004

(87) PCT Pub. No.: WO02/092816

PCT Pub. Date: Nov. 21, 2002

(65) Prior Publication Data

US 2004/0197308 A1    Oct. 7, 2004

(30) Foreign Application Priority Data

May 14, 2001   (JP) ............................. 2001-143999

(51) Int. Cl.
*C07H 21/02*   (2006.01)
*C07H 21/04*   (2006.01)
*A61K 31/70*   (2006.01)

(52) U.S. Cl. ................... 536/23.1; 536/24.1; 514/44
(58) Field of Classification Search ............... 536/23.1, 536/24.1; 514/44
See application file for complete search history.

(56) References Cited

U.S. PATENT DOCUMENTS 5,728,379 A * 3/1998 Martuza et al. ............ 424/93.2
6,613,563 B1 * 9/2003 Sosnowski et al. ........ 435/320.1

FOREIGN PATENT DOCUMENTS

WO   WO 96/34969   11/1996
WO   WO 98/35028   8/1998

OTHER PUBLICATIONS

Cross SH, Charlton JA, Nan X, Bird AP, Purification of CpG islands using a methylated DNA binding column, 1994, Nat Genet 6: 236-244.*
GenBank Accession No. Z54537, Oct. 16, 1995, National Center of Biotechnology Information, version Z54537.1, Locus: HS12H4R.*
Borisy et al., Proc Natl Acad Sci USA, 2003, 100: 7977-7982.*
El-Aneed et al., European Journal of Pharmacology, 2004, 498: 1-8.*
Keith et al., Nature Reviews, 2005, 4: 1-8.*
Everts et al., Cancer Gene Therapy, 2005, 12: 141-161, Review.*
Meng et al., Gene Therapy of Cancer, Chapter 1, 1999, pp. 3-20.*
Van Dyke et al., Cell, 2002, 108: 135-144.*
Jin, First Alberta Gene Therapy Meeting, Nov. 1995, p. 2, Abstract.*
Chung et al., J Virol, 1999, 73: 7556-7564.*
Miettinen et al., Modern Pathology, 1999, 12: 756-762.*
Tripathy et al., Proc Natl Acad Sci USA, 1994, 91: 11557-11561.*
Miano et al., J. Biol. Chem., 1996, 271: 7095-7103.*
H. Yamamura et al, "Identification of the Transcriptional Regulatory Sequences of Human Calponin Promoter and Their Use in Targeting a Conditionally Replicating Herpes Vector to Malignant Human Soft Tissue and Bone Tumors," Cancer Research, vol. 61, pp. 3969-3977, May 15, 2001.
K. Takahashi et al, "The .5'-Flanking Region of the Human Smooth Muscle Cell Calponin Gene Contains a cis-Acting Domain for Interaction with a Methylated DNA-Binding Transcription Repressor," J. Biochem., vol. 120, pp. 18-21, 1996.

* cited by examiner

*Primary Examiner*—Ileana Popa
(74) *Attorney, Agent, or Firm*—Locke Lord Bissell & Liddell, LLP

(57) ABSTRACT

The present invention provides a cell-specific replication-competent vector system, which does not target normal cells. The vector system is constructed by linking a transcriptional initiation regulatory promoter region upstream of a viral replication-related gene that integrates the linked region into a viral DNA vector. The constructed vector, when introduced into malignant tumor cells, selectively injures only tumor cells or proliferating smooth muscle cells of tumor neovascular tissue due to the selective expression of the regulatory promoter region upstream of a viral replication-related gene. In particular, the present invention relates to a transcriptional initiation regulatory region of the human calponin gene that can selectively express in tumor cells or proliferating smooth muscle cells of tumor neovascular tissue. The present invention also relates to methods of constructing the cell-specific replication-competent vector system and to treatment methods using the vector system by introducing the vector system into particular living tissues or cells such as malignant tumors and the like.

5 Claims, 10 Drawing Sheets

Figure 1, A
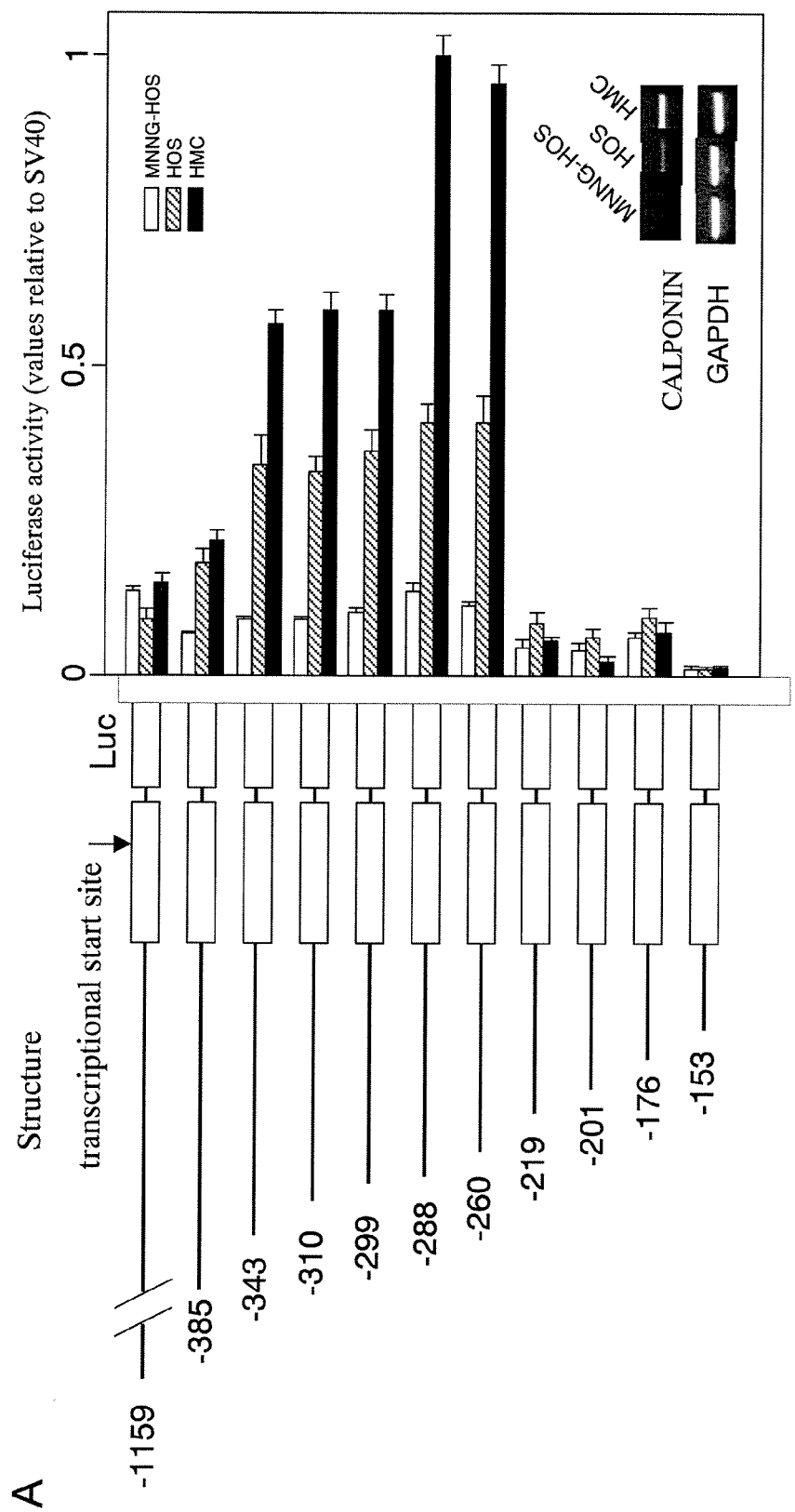

Figure 2, B
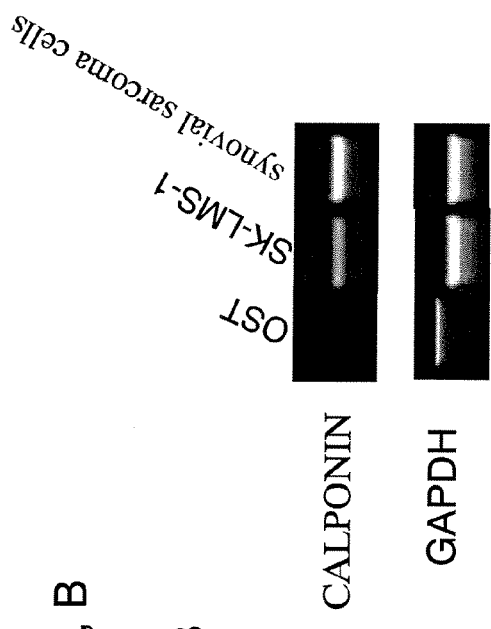
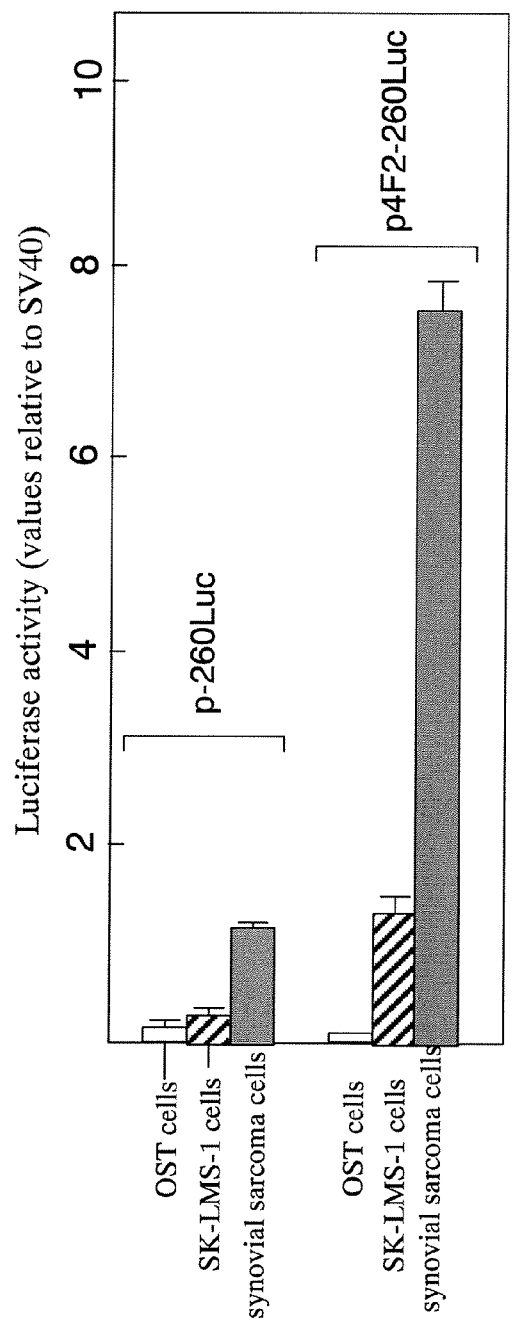

FIGURE 4
A Synovial Sarcoma
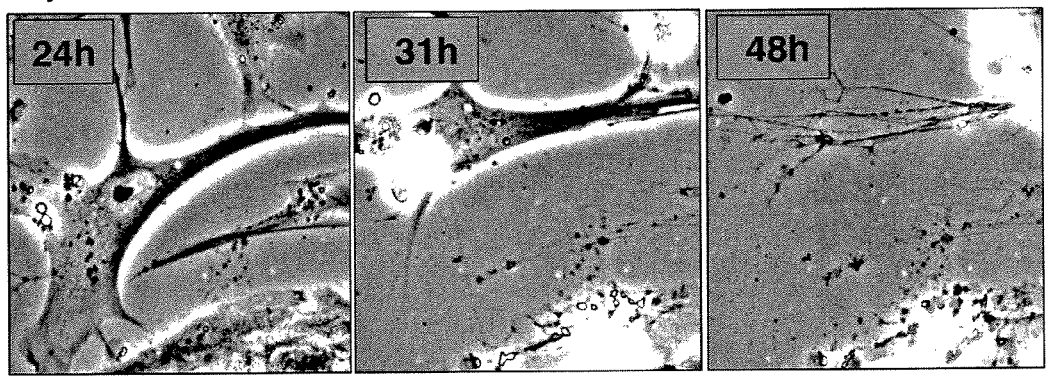
B SK-LMS-1 Leiomyosarcoma
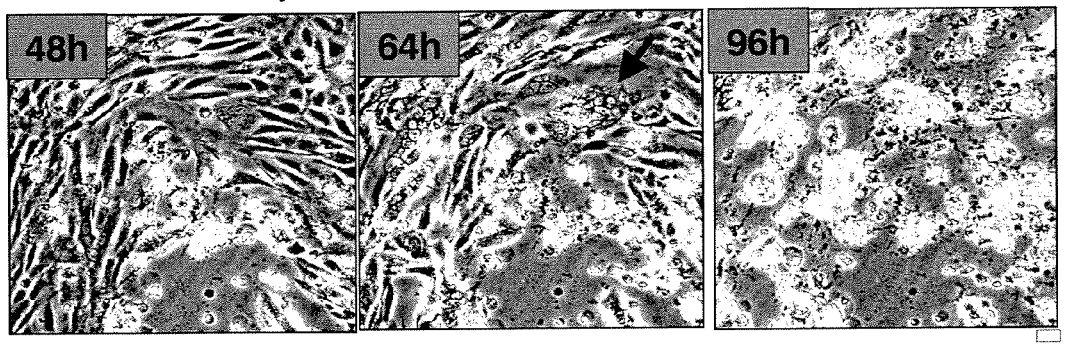

SK-LMS-1 Leiomyosarcoma

SEQUENCE LISTING

<160> NUMBER OF SEQ ID NOS: 17

<210> SEQ ID NO 1
<211> LENGTH: 41
<212> TYPE: DNA
<213> ORGANISM: Homo sapiens

<400> SEQUENCE: 1
gaaacaatga cacaatcagc tcccaatacc aagggcctga c          41

<210> SEQ ID NO 2
<211> LENGTH: 260
<212> TYPE: DNA

<213> ORGANISM: Homo sapiens

<400> SEQUENCE: 2

```
gaaacaatga cacaatcagc tcccaatacc aagggcctga catcacaagg ggaggggaag      60
gcagctgagg ttgtgggggg aggtgccccg ccccttggca ggcccctaca gccaatggaa     120
cggccctgga agagacccgg gtcgcctccg gagcttcaaa aacatgtgag gagggaagag     180
tgtgcagacg gaacttcagc cgctgcctct gttctcagcg tcagtgccgc cactgccccc     240
gccagagccc accggccagc                                                 260
```

<210> SEQ ID NO 3
<211> LENGTH: 333
<212> TYPE: DNA
<213> ORGANISM: Artificial Sequence
<220> FEATURE:
<223> OTHER INFORMATION: Description of Artificial Sequence: Region
      consist of human calponin gene promoter and its structural gene
      fragment

<400> SEQUENCE: 3

```
gaaacaatga cacaatcagc tcccaatacc aagggcctga catcacaagg ggaggggaag      60
gcagctgagg ttgtgggggg aggtgccccg ccccttggca ggcccctaca gccaatggaa     120
cggccctgga agagacccgg gtcgcctccg gagcttcaaa aacatgtgag gagggaagag     180
tgtgcagacg gaacttcagc cgctgcctct gttctcagcg tcagtgccgc cactgccccc     240
gccagagccc accggccagc atgtcctctg ctcacttcaa ccgaggccct gcctacgggc     300
tgtcagccga ggttaagaac aaggtagggg tgg                                  333
```

<210> SEQ ID NO 4
<211> LENGTH: 445
<212> TYPE: DNA
<213> ORGANISM: Homo sapiens

<400> SEQUENCE: 4

```
gtgagtgcag cgcgcccccg tcccgggtac ctccggttga atctggtggc ttgcaccgac      60
cccctcccct gtccccagac ggatctagat ggttcttccc tccatcccgt accgacgact     120
gtccccccctt cccccacccc ctcccccggca cattgtcctt ccctcctttc tttgaagaaa     180
gccgacccgc ccctcactcc gtcacgaggg tgggtgactc agcgtcctcc ttccccgcgg     240
cgccagaagc cagttgcaac cggtttctga agtaatgtgc aggactcctt acatcagctc     300
ctctgagtct cgtgattcag ccttgcctcc ctctctcccc ctttgccccc tccccgtccc     360
acccttaggc gctgggagaa gggagggtgg ggaggtcagg ggcctctcag aggggcctca     420
cttgttaacc cagcccccat ttcag                                           445
```

<210> SEQ ID NO 5
<211> LENGTH: 24
<212> TYPE: DNA
<213> ORGANISM: Artificial Sequence
<220> FEATURE:
<223> OTHER INFORMATION: FP1

<400> SEQUENCE: 5

```
gagtgtgcag acggaacttc agcc                                             24
```

<210> SEQ ID NO 6
<211> LENGTH: 21
<212> TYPE: DNA
<213> ORGANISM: Artificial Sequence -continued

```
<220> FEATURE:
<223> OTHER INFORMATION: RP1

<400> SEQUENCE: 6
gtctgtgccc aacttggggt c                                              21

<210> SEQ ID NO 7
<211> LENGTH: 20
<212> TYPE: DNA
<213> ORGANISM: Artificial Sequence
<220> FEATURE:
<223> OTHER INFORMATION: FP2

<400> SEQUENCE: 7
cccatcacca tcttccagga                                                20

<210> SEQ ID NO 8
<211> LENGTH: 21
<212> TYPE: DNA
<213> ORGANISM: Artificial Sequence
<220> FEATURE:
<223> OTHER INFORMATION: RP2

<400> SEQUENCE: 8
ttgtcatacc aggaaatgag c                                              21

<210> SEQ ID NO 9
<211> LENGTH: 18
<212> TYPE: DNA
<213> ORGANISM: Artificial Sequence
<220> FEATURE:
<223> OTHER INFORMATION: FP3

<400> SEQUENCE: 9
gacagccata tcctgagc                                                  18

<210> SEQ ID NO 10
<211> LENGTH: 22
<212> TYPE: DNA
<213> ORGANISM: Artificial Sequence
<220> FEATURE:
<223> OTHER INFORMATION: RP3

<400> SEQUENCE: 10
actcacagat cgttgacgac cg                                             22

<210> SEQ ID NO 11
<211> LENGTH: 19
<212> TYPE: DNA
<213> ORGANISM: Artificial Sequence
<220> FEATURE:
<223> OTHER INFORMATION: FP4

<400> SEQUENCE: 11
gagatgcgaa tatacgaat                                                 19

<210> SEQ ID NO 12
<211> LENGTH: 20
<212> TYPE: DNA
<213> ORGANISM: Artificial Sequence
<220> FEATURE:
<223> OTHER INFORMATION: RP4

<400> SEQUENCE: 12
gtgggtgggc tcggccaaat                                                20
```

```
<210> SEQ ID NO 13
<211> LENGTH: 19
<212> TYPE: DNA
<213> ORGANISM: Artificial Sequence
<220> FEATURE:
<223> OTHER INFORMATION: FP5

<400> SEQUENCE: 13
gcgttaccca acttaatcg                                                  19

<210> SEQ ID NO 14
<211> LENGTH: 18
<212> TYPE: DNA
<213> ORGANISM: Artificial Sequence
<220> FEATURE:
<223> OTHER INFORMATION: RP5

<400> SEQUENCE: 14
tgtgagcgag taacaacc                                                   18

<210> SEQ ID NO 15
<211> LENGTH: 20
<212> TYPE: DNA
<213> ORGANISM: Artificial Sequence
<220> FEATURE:
<223> OTHER INFORMATION: FP6

<400> SEQUENCE: 15
cccatcacca tcttccagga                                                 20

<210> SEQ ID NO 16
<211> LENGTH: 20
<212> TYPE: DNA
<213> ORGANISM: Artificial Sequence
<220> FEATURE:
<223> OTHER INFORMATION: RP6

<400> SEQUENCE: 16
ttgtcatacc aggaaatggc                                                 20

<210> SEQ ID NO 17
<211> LENGTH: 10
<212> TYPE: DNA
<213> ORGANISM: Homo sapiens
<220> FEATURE:
<221> NAME/KEY: misc_feature
<223> OTHER INFORMATION: GATA-1 consensus sequence

<400> SEQUENCE: 17
cacaatcagc                                                            10
```

REPLICATION VECTOR SHOWING CELL-SPECIFIC EXPRESSION

TECHNICAL FIELD

The present invention, in various embodiments, relates to a cell-specific replication-competent vector, which does not target normal cells and expresses a cell-specific gene capable of self-replicating; a DNA having activity to regulate gene expression that can be used for the construction of the vector; a method for expressing a gene in particular living cells using the inventive vector; and a method for disrupting particular cells, or the like.

More specifically, the present invention relates to, in one embodiment, the construction of a cell-specific replication-competent vector, which does not target normal cells, where the vector can express a gene in a cell-specific manner so as to disrupt tumor cells from proliferating. In another embodiment, the present invention relates to the field of gene therapy of tumors and the like. More specifically, the embodiment relates to the introduction of a gene to specific tumor cells for enabling treatment without injuring normal cells and to the construction of a cell disrupting vector.

BACKGROUND ART

Recently, an ideal treatment method for cancer, with minimal side effects, which does not affect normal cells but can selectively injure only cancer cells, is needed. For example, a gene therapy method that can enhance the selectivity of cancer cells in various levels, such as the cell selectivity of a gene to be inserted into cancer cells, the activity of an expression promoter, the method of introduction and infection of a virus vector, or the like, is regarded as a promising treatment method. However, a common problem of the existing methods is that the therapeutic gene cannot be introduced into all cancer cells.

On the other hand, concerning the immunocytic therapy of cancer, slight expression of a tissue-specific differentiation antigen has also been observed in normal tissue. Unfortunately, the expression in normal cells presents a problem. A cancer antigen based on a mutation has the disadvantage that this mutation is directed to the specific cancer, and it is therefore not appropriate to generalize it as an immunocytic therapy for cancer as a molecular target.

Recently, a clinical study was conducted in the United States and in Great Britain (*Gene Ther.* 7, 859-866, 2000; *Gene Ther.* 7, 867-874, 2000), respectively demonstrating gene therapy to treat malignant brain tumors using a replication-competent herpes simplex virus (HSV) vector, which selectively injures only the continuously growing cells by infection and replication. The replication-competent HSV vector is a vector wherein a ribonucleotide reductase (RR) or thymidine kinase (TK), essential to viral replication, is deleted. These enzymes are expressed only at the time of proliferation in normal cells, but are constitutively expressed in tumor cells. Thus, when the HSV vector infects actively proliferating cells, whether it is a normal cell or a tumor cell, the vector is replicated using cell-derived RR or TK, and shows cytolysis activity. Anti-tumor effects of a replication-competent HSV vector, with respect to prostate cancer and pancreatic cancer, have also been reported in animal experiments. (*J. Surg. Oncol.* 72, 136-141, 1999). However, these also do not have cell selectivity and the safety level is not high. Therefore, it could be used for treating tumor cells in the human brain, which has a blood brain barrier and where the vector does not diffuse into circulating blood. The problem is that this therapy is not appropriate for the treatment of organs other than the brain.

According to the discussion above, it is thought that if it were possible to control the injury activity of the HSV vector to target specific cells, it could be a more effective and safe treatment method. Miyatake and Martuza et al., of the United States, have reported a replication-competent HSV vector selective for liver tumor using an albumin promoter (*J. Virol.* 71, 5124-5132, 1997). However, when such a vector is used, the expression of the albumin gene decreases in liver cell carcinoma and also injures normal regenerated liver cells. Therefore, this treatment is considered to be inappropriate for clinical application in humans. Furthermore, Martuza and Miyatake have reported the possibility of this clinical application to mesothelioma in U.S. Pat. No. 5,728,379 ("Tumor- or cell-specific herpes simplex virus replication"), patented in March 1998. Notably, there is no description of the possible clinical application to human sarcoma in general, for example, leiomyosarcoma, osteosarcoma, and the like.

Gene analysis of the cause of disease and the pathology of sarcoma found a mutation of p53 and Rb and the existence of a fusion gene in some of the tumors, but the results are not yet at the stage to be applied widely for treatment. In an animal experiment using nude mice, Milas et al., have introduced the p53 gene into leiomyosarcoma cells, using an adenovirus vector that does not have the ability to replicate, and have reported delayed tumor proliferation (*Cancer Gene Ther.* 7, 422-429, 2000). Furthermore, a method for introducing and expressing thymidine kinase, a suicide gene, into osteosarcoma using a promoter of osteocalcin gene has been reported (*Cancer Gene Ther.* 5, 274-280, 1988). However, this method uses a virus vector where the ability to replicate is removed, and the efficiency of introducing the gene is low. Thus, this method cannot be applied to sarcoma other than osteosarcoma.

Especially, in the report of Milas et al., an example using the human smooth muscle cell line SK-LMS-1 is described. However, the number of viral particles used is more than 100 to 1000 times compared to the number of particles of virus vector used in the present invention. Thus, the effect is inferior compared to the example of the present invention. Therefore, the results of Milas, et al. are not preferable since the number of viral particles to be injected into the body should be minimal to reduce side effects.

Moreover, as for a therapy for suppressing vascularization of cancer, Folkman et al. have reported a dramatic anti-tumor effect of peptidergic inhibiting factors such as angiostatin, endostatin or the like, in mice experiments (*Cell* 79, 315-328, 1994; *Cell* 88, 277-285, 1997). Nakamura et al. have also reported the action to suppress vascularization of $NH_4$, which is a fragment of a liver cell growth factor molecule (*Biochem. Biophys. Res. Commun.* 279, 846-852, 2000). However, these methods are problematic and have problems such as, for example, a large required number of peptides; low endostatin reproducibility; unknown mechanism of action; and unconfirmed efficacy in humans, or the like. A vascularization inhibitor, now being clinically tested, does not have cell selectivity and has low inhibition efficiency. The peptide inhibiting integrin from acting on the surface of endothelial cells, which Cheresh et al. of the United States has reported, similarly does not have cell selectivity and the inhibition efficiency is low (*J. Clin. Invest.* 103, 1227-1230, 1999). All of these studies are directed to treatments where the target is a vascular endothelial cell. However, a therapeutic agent having cell selectivity targeting proliferating vascular smooth muscle cells in tumor vessels remains unknown. Actually, the antagonist of a platelet-derived growth factor receptor, which promotes the proliferation and the migration of smooth muscle cells, has been reported to have a strong tumor neovascular suppressing action (Cancer Res. 60, 4152-4160, 2000). The significance of attacking vascular smooth muscle cells to suppress tumor vascularization is being evaluated, but since this method is not cell specific, disadvantages or problems are anticipated.

On the other hand, the calponin gene, which is said to be a differentiated marker of smooth muscle, was found to be expressed in tumor cells of human-derived sarcoma (Int. J. Cancer 79, 245-250, 1998; Sarcoma 3, 107-113, 1999; Intern. J. Cancer 82, 678-686, 1999). Many reports have been subsequently made, indicating that the calponin gene is expressed abnormally in about 20 kinds of human malignant tumors derived from mesenchymal cells, such as gastrointestinal stromal tumor (GIST), salivary gland sarcoma, fibrosarcoma, malignant neurilemmoma and the like, in addition to sarcoma in the bone and soft parts. The calponin gene mentioned above (h1 or basic) has been shown by X-ray crystallography and in vitro and in vivo mechanism analyses to suppress the sliding movement of actin/myosin by binding to the C-terminus of the actin molecule (Biochem. Biophys. Res. Commun. 279, 150-157, 2000; J. Physiol. 529, 811-824, 2000). The calponin gene is considered to be selectively expressed in smooth muscle cells of an adult and is a differentiated marker in blood vessels (Physiol. Rev. 75, 487-517, 1995).

BRIEF SUMMARY

One object of the present invention is to construct a cell-specific replication-competent vector to use for treating malignant tumors and the like, which expresses and replicates a specific gene in certain cells such as malignant tumors and the like, without injuring normal cells. Another object is to provide a DNA having gene expression regulatory activity. Yet another object is to provide a method of treatment by introducing and expressing the cell-specific replication-competent vector into certain living cells such as malignant tumors and the like, etc.

The objectives mentioned above have been elucidated. A cell-specific replication-competent vector has been constructed, which does not target normal cells, and that can induce viral replication by the following: by obtaining a transcriptional initiation regulatory region from particular tumor cells or smooth muscle cells of the human calponin gene, which is expressed specifically in these cells; by integrating upstream of the gene that encodes a transcription factor necessary to start replication of a viral replication-related gene; by substituting it with a TK gene which is an enzyme essential to the replication of viral DNA; and by expressing this gene in particular cells such as malignant tumor cells or proliferating smooth muscle cells in new blood vessels in tumors and the like. By introducing this cell-specific replication-competent vector into a malignant tumor tissue, specific tumor cells or tumor neovascular proliferating smooth muscles are injured.

BRIEF DESCRIPTION OF DRAWINGS

FIG. 1 shows the transcriptional activity when a 5' deleted F mutant of the calponin gene promoter is transfected.

FIG. 2 shows the effect of an enhancer at a transcriptional level in a regulatory region controlling human calponin expression in calponin-positive tumor cells.

FIG. 4 shows the injury effect of tumor cells by d12.CALP in vitro.

DISCLOSURE OF THE INVENTION

Figure 3:
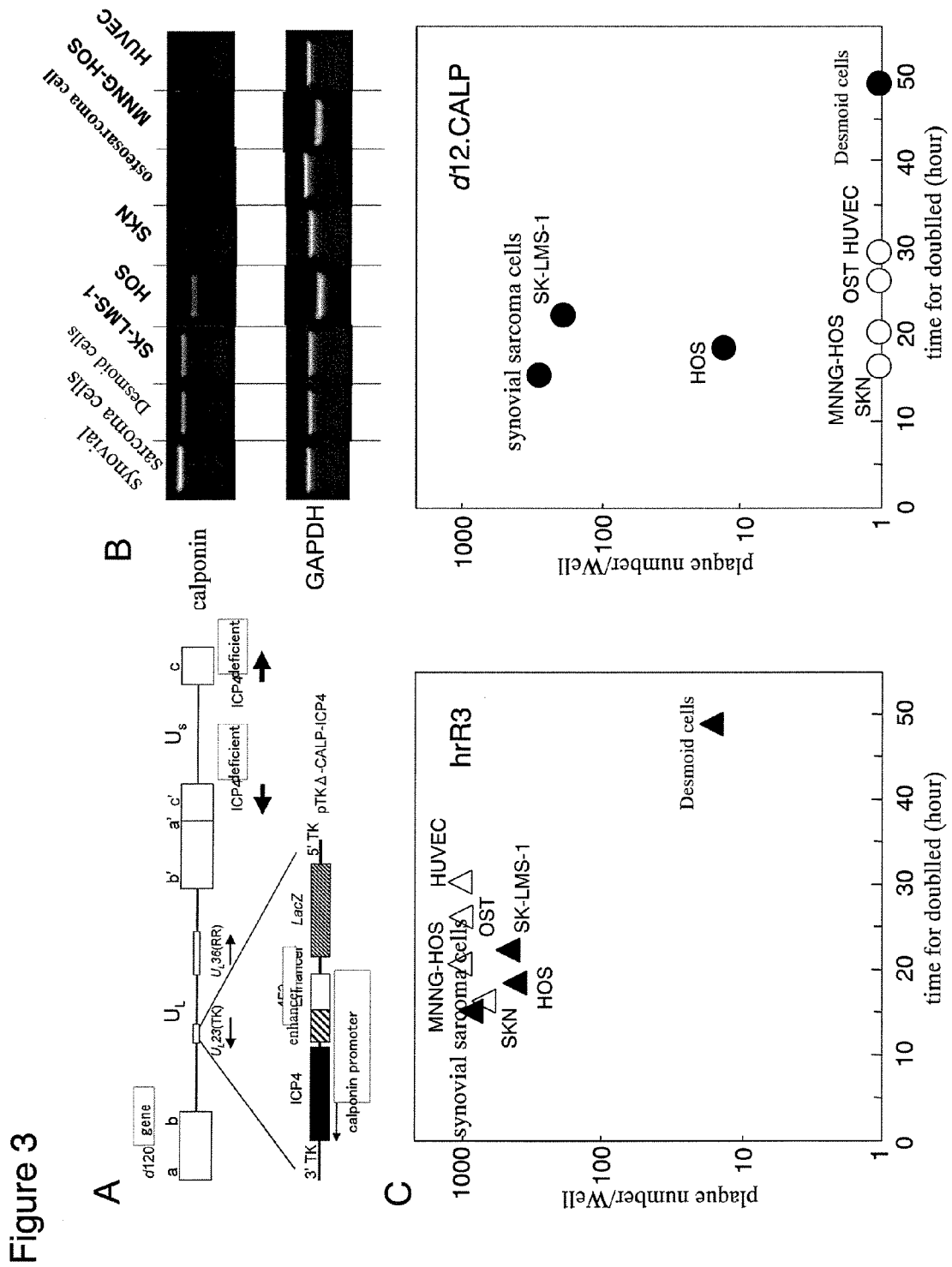
FIG. 3 shows the structure of d12. CALP and the results of the cytopathic assay in vitro.

The present invention, in one embodiment, relates to a cell-specific replication-competent vector, which does not target normal cells. Another embodiment relates to the cell-specific replication-competent vector where a transcriptional initiation regulatory region of a gene specifically expressed in cells is integrated upstream of a predetermined gene; where the transcriptional initiation regulatory region of a gene specifically expressed in cells is a region including a base sequence of Seq. ID No. 1; where the region including the base sequence of Seq. ID No. 1 is a region including a human calponin gene promoter having a base sequence of Seq. ID No. 2; where the region including the base sequence of Seq. ID No. 2 is a region including a base sequence of Seq. ID No. 3; where the transcriptional initiation regulatory region of a gene specifically expressed in cells comprises a base sequence; where one or a few bases are deleted, substituted or added in the base sequence of Seq. ID No. 1, Seq. ID No. 2, or Seq. ID No. 3, and is a region including a base sequence having an activity to regulate transcriptional initiation; where an enhancer is integrated upstream of the transcriptional initiation regulatory region; where the enhancer is an 4F2 enhancer; where the predetermined gene is a viral replication-related gene; where the viral replication-related gene is a gene that encodes a transcription factor essential to start viral replication (ICP4); where an apoptosis-related gene is linked further downstream of the predetermined gene, and expressed under the control of the transcriptional initiation regulatory region and the enhancer; where a DNA that encodes a protein having action to suppress vascularization is linked further downstream of the predetermined gene, and expressed under the control of the transcriptional initiation regulatory region and the enhancer; where a DNA that encodes a protein having action to suppress cancer metastasis is linked further downstream of the predetermined gene, and expressed under the control of the transcriptional initiation regulatory region and the enhancer; where a DNA that encodes a protein having action to suppress cancer is linked further downstream of the indicated gene, and expressed under the control of the transcriptional initiation regulatory region and the enhancer; the cell-specific replication-competent vector, where the replication-competent vector is a viral vector; the cell-specific replication-competent vector, where the virus vector is a herpes simplex virus vector (HSV vector) or an adenovirus vector; the cell-specific replication-competent vector, where the vector is a replication-competent vector specific to tumor cells and specific to proliferating smooth muscles of new tumor blood vessels; where a DNA that encodes ribonucleotide reductase and/or a DNA that encodes thymidine kinase is deleted.

Furthermore, embodiments of the present invention relate to a DNA having a base sequence of Seq. ID No. 1 or its complementary sequence; a DNA having a base sequence of Seq. ID No. 2 or its complementary sequence; a DNA having a base sequence of Seq. ID No. 3 or its complementary sequence; a DNA having a base sequence where one or a few bases are deleted, substituted or added in a base sequence of Seq. ID No. 1, Seq. ID No. 2 or Seq. ID No. 3 and has a base sequence having an activity regulating transcriptional initiation or its complementary sequence; a DNA having a base sequence of Seq. ID No. 1, Seq. ID No. 2 or Seq. ID No. 3, or a base sequence where one or a few bases are deleted, substituted or added in a base sequence of Seq. ID No. 1, Seq. ID No. 2 or Seq. ID No. 3 and has a base sequence where an enhancer sequence is integrated upstream of a base sequence having an activity to regulate transcriptional initiation or its complementary sequence; a DNA, where the enhancer is a 4F2 enhancer.

Moreover, embodiments of the present invention relate to a method for expressing and replicating a gene, a protein or a peptide of a cell-specific replication-competent vector, which does not target normal cells, by introducing the cell-specific replication-competent vector, into a living cell or tissue, to express and replicate; the method for expressing and replicating a gene, a protein or a peptide of the cell-specific replication-competent vector, where the living cell or tissue is a tumor tissue; a therapeutic drug having the cell-specific replication-competent vector, which does not target normal cells; the therapeutic drug characterized by being a therapeutic drug against malignant tumor; a method for treating malignant tumors where the cell-specific replication-competent vector, which does not target normal cells is introduced into a tumor tissue, to express a predetermined gene, protein or peptide; a method for treating malignant tumors where the cell-specific replication-competent vector, which does not target normal cells is introduced into a tumor tissue, to express a predetermined gene, protein or peptide; and selectively disrupts only tumor cells, a method for treating malignant tumors where the cell-specific replication-competent vector, which does not target normal cells is introduced into a tumor tissue, to express a predetermined gene, protein or peptide, and selectively disrupts only proliferating smooth muscles cells surrounding blood vessels of new tumor blood vessels.

BEST MODE OF CARRYING OUT THE INVENTION

As for the cell-specific replication-competent vector, which does not target normal cells, there is no specific limitation as long as it is a vector in which a transcriptional initiation regulatory region of a gene, specifically expressed in cells, is integrated upstream of a predetermined gene. However, it is preferable for it to be a replication-competent vector specific to tumor cells and specific to proliferating smooth muscle cells of new tumor blood vessels. As for the transcriptional initiation regulatory region of the gene specifically expressed in cells, a promoter region of the gene specifically expressed in these cells or a region of a part of this promoter can be exemplified, and more concretely, the examples include: a region including a base sequence from −260 to −219 of a calponin gene promoter of Seq. ID No. 1; a human calponin gene promoter having a base sequence of Seq. ID No. 2; a human calponin gene promoter having a base sequence of Seq. ID No. 3 and a region including a part of its structural gene. Furthermore, as for the transcriptional initiation regulatory region of a gene specifically expressed in cells, a base sequence where one or a few bases are deleted, substituted or added in the above-mentioned base sequence of Seq. ID No. 1, Seq. ID No. 2 or Seq. ID No. 3, having a regulating activity of transcriptional initiation, for example a region including a homologous region to a calponin promoter derived from mouse, rat and pig can be exemplified.

As for the transcriptional initiation regulatory region of a gene specifically expressed in cells, other than the above mentioned, when proliferating smooth muscle cells are made the target of attack, the promoter region of the SM22α gene (the sequence from −480 to −26 of the human SM22α gene; its homologous region of the SM22α gene derived from GenBank accession #D84342-D84344 mouse, rat or other mammals) may be used, and when endothelial cells are made the target of attack, a promoter region of Flk-1 or a promoter region of the Flk-1 gene may be used. In these cases, a region including a part of a structural gene may also be made the transcriptional initiation regulatory region.

Another embodiment relates to linking an enhancer which significantly activates transcription upstream of a transcriptional initiation regulatory region of a gene specifically expressed in the cells mentioned above. As for this enhancer, there is no specific limitation as long as it is an enhancer such as an enhancer of an adenovirus early gene, an enhancer of Moloney murine leukemia virus long terminal repeat, an enhancer of histone H2A gene, an enhancer of immunoglobulin, an enhancer of an insulin gene, an enhancer of a c-fos gene, an enhancer of T-cell antigen receptor gene, an enhancer of a myopathic creatine kinase gene, a transcriptional enhancer of a human 4F2 heavy-chain and the like. However, in the case where the transcriptional initiation regulatory region of a gene specifically expressed in cells is a region including a sequence from −260 to +73 of a promoter of a calponin gene, a 4F2 enhancer such as human 4F2 heavy-chain transcriptional enhancer (Seq. ID No. 4) the enhancer of a 4F2 heavy-chain gene, which is a membrane type-II glycoprotein, crossing the transmembrane structure only once and is believed to be an activating factor of an amino acid transporter, which enhances the transcription efficiency significantly.

As for the predetermined gene useful for the construction of the cell-specific replication-competent vector, which does not target normal cells, there is no specific limitation as long as it is a gene necessary to start or maintain viral replication. For example, a viral replication-related gene such as E1A gene of adenovirus, ICP6 (ribonucleotide reductase) gene and the like can be exemplified, and a gene that encodes a transcription factor necessary to start the replication of herpes virus (ICP 4). Furthermore, as for these genes, it may be a gene where a part or all of the original structural gene located downstream of the transcriptional initiation regulatory region is bound with the above mentioned predetermined gene inframe, and a DNA that encodes a fusion protein of a part of the N-terminal side of calponin protein with ICP4 protein can be exemplified.

The cell-specific replication-competent vector, which does not target normal cells, has one or more than two apoptosis-related genes, DNA that encodes a protein having an action to suppress vascularization, DNA that encodes a protein having an action to suppress cancer metastasis, or DNA that encodes a protein having an action to suppress cancer and the like are linked further downstream of the predetermined gene, and can be expressed under the control of the transcriptional initiation regulatory region and where an enhancer may be used. Examples of the apoptosis-related gene mentioned above include: an apoptosis-promoting gene such as Bcl-xs, Bok/Mtd, Bcl-Gs/Bra, Bcl-GL, Bcl-Rambo, Hrk/DP5, Bik/Nbkblkbad, Bid, BimL, S, EL/BodL, M, S, Noxa/APR, Puma and the like; examples of DNA that encodes a protein having an action to suppress vascularization include: DNA that encodes a protein such as angiostatin, endostatin, FLK1, FLT1, FLT4, Tie1, Tie2 and the like; examples of the DNA that encodes a protein having an action to suppress cancer metastasis include: DNA that encodes a protein such as matrix metalloprotease (MMP) inhibitor, bovine lactoferrin (bLF) and the like; examples of DNA that encodes a protein having an action to suppress cancer include DNA that encodes materials suppressing cell cycle such as p21, p16, p15, p53 and the like or materials suppressing cell proliferation such as p53, Rb, IRF-1, APC and the like, but they are not limited to these examples.

As for the backbone of the virus vector used for the construction of the cell-specific replication-competent vector which does not target normal cells, it can be a vector that can be expressed by being infected in tumor cells such as sarcoma in bone and soft parts, leiomyosarcoma, gastrointestinal stromal tumor (GIST), malignant mesothelioma, malignant fibrous histiocytoma, fibrosarcoma, malignant meningioma, neurilemmoma and the like, or proliferating smooth muscle cells or cells around vessels of new tumor blood vessels, or introduction in a gene. As for the vector, an expression vector derived from a chromosome, an episome, a liposome and a virus can be exemplified. However, a virus vector including papovavirus such as SV40, vaccinia virus, adenovirus, adeno-associated virus vector, vector derived from fowl pox virus, pseudorabies virus, retrovirus, herpes simplex virus vector (HSV vector) and the like maybe preferable, and among these, HSV vector and adenovirus vector, especially a conditionally replication-competent HSV vector or a conditionally replication-competent adenovirus vector maybe preferable from the point of view of the high efficiency of gene expression, the cytotoxic activity specific to proliferating cell, or the like. Using, for example, a DNA that encodes ribonucleotide reductase, a DNA that encodes thymidine kinase or a vector where both of these are deleted as the conditionally replication-competent HSV vector mentioned above, the cell-specific replication-competent vector, which does not target normal cells, may be preferably constructed.

As for a DNA, which can be the object of the present invention, there is no specific limitation as long as it is a DNA having a base sequence of Seq. ID No. 1 or its complementary sequence; a DNA having a base sequence of Seq. ID No. 3 or its complementary sequence; or a DNA having a base sequence where one or a few bases are deleted, substituted, or added in a base sequence of Seq. ID No. 1, Seq. ID No. 2 or Seq. ID No. 3, and having a base sequence having a regulating activity of transcriptional initiation, for example, a homologous sequence of a calponin gene derived from mammals such as mouse, rat or pig and the like, or its complementary sequence. However, preferably, a DNA having: a base sequence of Seq. ID No. 1; a base sequence shown An Seq. ID No. 2; a base sequence of Seq. ID No. 3; or a sequence having a base sequence where one or a few bases are deleted, substituted or added in a base sequence of Seq. ID No. 1, Seq. ID No. 2 or Seq. ID No. 3, and an enhancer sequence is integrated upstream of a base sequence and the like, having a regulating activity of transcriptional initiation, or their complementary sequence can be exemplified. Furthermore, as for the enhancer sequence, the known enhancer sequences, preferably a 4F2 enhancer sequence such as a human 4F2 heavy-chain transcriptional enhancer and the like having a base sequence of Seq. ID No. 4 can be exemplified.

As for the method of expressing and replicating the cell-specific replication-competent vector, which does not target normal cells, there is no specific limitation. As long it is a method of expressing and replicating by directly introducing the cell-specific replication-competent vector, which does not target normal cells into a living cell or tissue, such as a tissue or organ where a tumor such as sarcoma in bone and soft parts, leiomyosarcoma, gastrointestinal stromal tumor (GIST), malignant mesothelioma, malignant fibrous histiocytoma, fibrosarcoma, malignant meningioma, neurilemmoma and the like, or by injecting cell-specific replication-competent vector into a vascular system that nourishes the tumors. In the case that the proliferating smooth muscle cells of new tumor blood vessels is made the target of attack, a method for expressing and replicating by directly introducing or injecting cell-specific replication-competent vector into a vascular system that nourishes the tumors regardless of the type of malignant solid tumor. Moreover, as for the therapeutic drug of the present invention, it can be of any kind as long as it comprises the cell-specific replication-competent vector, which does not target normal cells, as an active ingredient, and it is preferable that the therapeutic drug is a therapeutic drug against living cells or tissues, preferably against the malignant tumors mentioned above.

Moreover, as for the treatment method of malignant tumors, there is no specific limitation as long as it is a method for introducing the cell-specific replication-competent vector which does not target normal cells into a tumor tissue to express a predetermined gene, protein or peptide. Among these, a method for selectively disrupting only a tumor cell or a method for selectively disrupting only proliferating smooth muscle cells or cells surrounding blood vessels of new tumor blood vessels can be useful. As for the method for introducing into a tissue where a malignant tumor is generated, a method of introducing directly the cell-specific replication-competent vector mentioned above into malignant cells, or a method for injecting into a vascular system that perfuses in a tumor may also be useful and exemplified.

Embodiments of the present invention will be explained more specifically in the following with reference to the examples, while the scope of the invention will not be limited to these examples.

EXAMPLE A

Methods and Materials

A-1 (Cells, Culture Methods, Antibodies and Viruses)

Human leiomyosarcoma cell lines SK-LMS-1 (HTB-88), human osteosarcoma cell lines HOS(CRL-1543), MNNG-HOS(CRL-1547), and Vero cells (CCL-81) were purchased from American Type Culture Collection. Human leiomyosarcoma cell line SKN (RCB0513) and human osteosarcoma cell line OST (RCB0454) were purchased from RIKEN GENE BANK. Human synovial sarcoma and desmoid tumor cell lines were established from resected tumor samples from patients of each tumor. Diagnosis of synovial sarcoma was conducted as described previously (Sarcoma 3, 107-113, 1999), by confirming the expression of the SYT-SSX fusion gene. Primary cultured human mesanglum cells (HMC; provided by Dr. Yamabe, Hirosaki University School of Medicine; Nephrol. Dial. Transplant. 12, 438-442, 1997) were prepared from the kidneys of human fetuses (16 or 18 weeks of gestation)(established by Dr. M. R. Daha, University Hospital of Leiden), subcultured 4 to 6 times, and then used in the following example. Human umbilical vein endothelial cell line HUVEC (T200-05) were purchased from TOYOBO Biochemicals. Vero cells where ICP4 gene was introduced and E5 cells were provided by N. Deluca (University of Pittsburgh School of Medicine, Pittsburgh) for use. SK-LMS-1 was cultured in Eagle's MEM supplemented with 1 mM sodium pyruvate. HOS, MNNG-HOS; OST, Vero cells and ES cells were cultured in DMEM. SKN cells were cultured in F12 medium. Synovial sarcoma cells and desmoid tumor cells were cultured in RPMI 1640 medium. Human mesangium cells were cultured in DMEM added with 1 mg/ml D-glucose. All media contain the following respectively: 10%, 15% (for SKN) or 20% (for synovial sarcoma cells and desmoid cells) in final concentration of heat-inactivated fetal bovine serum (Upstate Biotechnologies); 2 mM L-glutamine; 100 units/mL penicillin; and 100 μg/mL streptomycin. HUVEC were cultured in a medium according to the manufacturer's instructions. Furthermore, all cells mentioned above were cultured at 37° C. in a humidified atmosphere containing 5% $CO_2$.

A polyclonal antibody specific to mouse calponin (basic or h1) was prepared in the same manner as described previously (*Genes to Cells* 3, 685-695, 1998). A monoclonal antibody to HSV-1 or HSV-2 ICP4 protein (clone No. 1101) was purchased from the Goodwin Institute for Cancer Research. Immunoblot analysis was carried out in the same manner as described previously (*Int. J. Cancer* 79, 245-250, 1998). Chemiluminescence (ECL; Amersham Pharmacia Biotech) was used to visualize the bound antibodies, according to the manufacturer's protocol. Moreover, ICP4 deletion mutant of HSV, d120 (*J. Virol.* 56, 558-570, 1985) and 1096 (ribonucleotide reductase)-deletion mutant of HSV, hrR3, provided by N. Deluca or Dr. S. Weller (University of Connecticut Health Center, Farmington), respectively were generated from low-multiplicity infections to E5 cells or Vero cells, respectively.

A-2 (RNA Preparation and RT-PCR Analysis)

Total RNA was extracted respectively from cells or tissues cultured using the Isogene RNA extraction kit (Nippon Gene), and subjected to semi-quantitative RT-PCR analysis as described previously (*Int. J. Cancer* 79, 245-250, 1998). The conditions for the PCR amplification were: denaturation at 94° C. for 40 seconds, annealing at 60° C. for 30 seconds, extension reaction at 72° C. for 90 seconds; and the cycle was repeated 30 times. As a human calponin primer, 5'-gagtgtg-cagacggaacttcagcc-3' [forward primer 1(991); nt#10-33 GenBank D17408; Seq. ID No. 5] and 5'-gtctgtgcccagcttgggtc-3' [reverse primer 1 (RP1); nt#660-680; Seq. ID No.6] were used; as a primer of GAPDH (glyceraldehyde 3-phosphate dehydrogenase) as a control, 5'-cccatcaccatcttccagga-3' [forward primer 2 (FP2); nt#342-360; Seq. ID No.7] and 5'-ttgt-cataccaggaaatgagc-3' [reverse primer 2 (RP2); nt#1052-1070; Seq. ID No. 8] were used to amplify the DNA of 671 bp and 731 bp, respectively.

A-3 (Isolation of the Human Calponin Promoter)

Genomic clones containing the 5' upstream end of the human calponin gene were isolated by screening a human genomic AEMBL3 phage library as previously described (*J. Biochem.* 120, 18-21, 1996). The 5' end-deleted fragments, p-1159Luc, p-385Luc, p-343Luc, p-310Luc, p-299Luc, p-288Luc, p-260Luc, p-239Luc, p-219Luc, p-201Luc, p-176Luc, p-153Luc were generated by PCR amplification, and then subcloned into a pGL2-Basic vector (Promega). Numbers indicate the 5' end of the DNA fragments are upstream from the ATG translational initiation codon, hereinafter referred as +1. These deletion fragments have a common 3' end at position +73. The nucleotide sequence of the cloned fragments was determined using a DQS-2000L DNA sequencer (SHIMADZU) according to the manufacturer's protocol, and it was confirmed that the sequence was identical to the sequence (DDBJ/GenBank™/EMBL database; accession No. D85611) described previously (*J. Biochem.* 120, 18-21, 1996).

A-4 (Transfection and Luciferase Analysis)

Cells cultured beforehand were divided and sprayed on a plate 24 hours before transfection. Cells ($5 \times 10^4$) were transfected by injecting in a 6-well dish, 1.2 μg of the promoter plasmid, 0.3 μg of the pCAGGS/β-gal reference plasmid, 3.75 μl of FuGENE~6 transfection reagent (Roche) in each well, according to the manufacturer's protocol. Twenty-four hours after transfection, the cells were harvested in 100 μl/well of the cell lysis buffer (PicaGene™ Luciferase Assay System, Toyo Ink). After centrifugation at 4° C. at 12000 g for 5 minutes, the supernatant (20 μl or 30 μl) was used for a luciferase assay and β-galactosidase assay, respectively. Luciferase activity was measured using a BLR-201 luminescence reader (Aloka). galactosidase assay was carried out using a β-galactosidase enzyme assay system (Promega) as previously described (*J. Biochem.* (Tokyo) 122, 157-167, 1997). All experiments were repeated at least three times to check reproducibility. By assaying cell extracts for β-galactosidase activity, the transfection efficiency was determined, and luciferase activities (light units) were corrected according to the value. By comparing expression of the pSV2-Luc gene containing the SV40 enhancer and SV40 promoter, transfection efficiency of different cell lines was estimated. Data are expressed as % normalized light units±S.E. relative to the values of pSV2-Luc.

A-5 (Virus Preparation)

A 4.1 kb blunt-ended SalI-MseI fragment (provided by Dr. Hayward, Johns Hopkins School of Medicine) derived from pGH108 (*J. Virol.* 56, 558-570. 1985) containing an ICP4 coding region, was subcloned into the blunt-ended Hind III site of the pAMP1 vector downstream of the 333 bp human calponin promoter (−260 to +73) at the cloning region and the 444 bp NotI fragment of the human 4F2 heavy-chain transcriptional enhancer (Mol. Cell. Biol. 9, 2588-2597, 1989) (provided by Mr. Leiden, Harvard Medical School) at the SmaI site of the vector. The pAMP1/CALP-ICP4 vector was double digested with SalI and Hind III, and the resulting 4.7 kb fragment was subcloned into the blunt-ended Xba1 site of the pTKΔL recombinant vector. The pTKΔL recombination vector contains the TK coding sequence with a deletion of the 0.5 kb BglII-KpnI region, *Escherichia coli*-derived LacZ, and SV40-derived poly A signal site upstream of the TK sequence (+53 of TK) (*J. Virol.* 71, 5124-5132, 1997). Linearized pTKΔ-CALP-ICP4 at SalI site in the plasmid backbone and d120 DNA were co-transfected into 55 cells using Lipofectamine™ (GIBCO/BRL), according to the manufacturer's protocol. Recombinant virus vectors d12.CALP identified as a single plaque, were stained blue with 5-bromo-4-chloro-3-indolyl-β-D-galactopyranoside(X-gal) agarose overlay, and were plaque purified three times by infecting into E5 cells in the presence of gancyclovir (1 μ/l). DNA was purified and resolved with restriction enzymes, and the recombination was confirmed by Southern blot and PCR analysis.

Viruses were prepared by infecting 10 to 20 150 $cm^2$/tissue culture flasks (IWAKI CLASS) of E5 cells, and harvesting the detached cells after 48 hours. Cells were collected by centrifugation at 4° C. for 5 minutes at 400×g, and were suspended in 10 ml of cold virus buffer (20 mM Tris-HCl, pH 7.5 containing 150 mM NaCl). The cells were lysed with three cycles of freezing and thawing in combination with sonication (6 times for 1 minute). After centrifugation at 4° C. for 5 minutes at 1500×g, the supernatant was further centrifuged at 4° C. for 45 minutes at 15000×g. The resulting pellet was suspended in the cold virus buffer, and titers of purified d12.CALP were determined by plaque assay on E5 cells.

A-6 (In Vitro Cytopathic Assay and Viral Replication Assay)

Viruses were infected onto subconfluent monolayers in a 6-well tissue culture plate at a multiplicity of infection (MOI) of 0.01 or 0.001 pfu/cell in 1% heat inactivated FBS/PBS. These infected cells were incubated at 37° C. for 1 hour, and then cultured in a medium containing 1% FBS and 11.3 µg/ml human IgG (Jackson ImmunoResearch Lab.). Forty-eight hours after infection, the number of plaques/well were counted. For viral replication assay, monolayer cultures of SK-LMS-1 cells or OST cells in 12-well tissue culture plates ($2\times10^5$ cells/well) were infected with d12.CALP at a multiplicity of infection (MDI) of 0.1 in 1% FBS/PBS. The virus inoculum was removed after 1 hour, and the above-mentioned cells were incubated in the medium. The infected virus was harvested from the wells at the predetermined time (12 hours, 24 hours and 48 hours) with 100 µl of the virus buffer. The cell lysates (1 µl) were diluted to $10^{-3}$, $10^{-4}$ and $10^{-5}$, and then titers of the viruses were determined from E5 cells.

For immunoblot analysis of ICP4 expression, SK-LMS-1 cells and OST cells were infected with d12.CALP at a multiplicity of infection (MOI) of 0.01 or the virus buffer alone, and was harvested after 22 hours of culture. Equal amounts of proteins were electrophoresed in a 9% SDS-PAGE gel, and transferred to a nitrocellulose membrane (Bio-Rad). Membranes were blocked with 5% skim milk (DIFCO Laboratories) for 2 hours at room temperature, and then incubated with anti-ICP4 antibody (dilution ratio 1:500) at 4° C. overnight.

A-7 (In Vivo Treatment and Histological Analysis)

SK-LMS-1 cells or OST cells were injected subcutaneously into the flanks of 6 week-old female athymic nude mice (BALB/c S1C-nu/nu)(Nihon SLC), to settle the tumors. The tumors were grown in the nude mice to about 6 to 7 mm in diameter. 50 µl (per tumor volume of 100 mm³) of virus suspended solution containing $1\times10^7$ pfu of d12.CALP or an equal amount of virus buffer was injected into the tumors using a 30-gauge needle, respectively. The same operation was repeated 9 days later. The tumors were measured at the predetermined times after injection, and tumor volumes were calculated using the formula [$0.53\times$length$\times$width$^2$]. In the experiments testing whether d12.CALP can be directed to tumors at the opposite side, SK-LMS-1 xenografts were settled beneath the skin in the flanks of both sides of 6-week-old male nude mice, and the viruses were injected into the tumor at one side.

For histological studies, $1\times10^7$ pfu/tumor volume of 100 mm³ of d12.CALP was administered once, and then the nude mice with tumors were sacrificed on the predetermined days. The subcutaneous tumors were removed and fixed with 2% paraformaldehyde, 0.5% glutaraldehyde, in PBS containing 1 mM $MgCl_2$ overnight at 4° C. Then, the tumors were placed in a substrate solution, containing X-gal (1 mg/ml), 5 mM $K_3Fe$ $(CN_6)$, 5 mM $K_4Fe$ $(CN_6)$ and 1 mM $MgCl_2$ in PBS for 3 hours at 37° C., and washed with PBS containing 3% DMSO.

To assess the distribution of infected viruses by PCR, DNA was prepared from fresh tissues of infected or non-infected tumors, and brain, lung, liver, kidney, heart, small intestine and uterus or testis. The conditions for PCR amplification were: denaturation at 94° C. for 40 seconds, annealing at 60° C. for 30 seconds, extension reaction at 72° C. for 90 seconds, and the cycle was repeated 30 times. As for ICP6 (ribonucleotide reductase) primer, 5'-gacagccatatcctgagc-3' [forward primer 3 (FP3); Seq. ID No. 9] and 5'-actcacagatcgttgac-gaccg-3' [reverse primer 3 (RP-3); Seq. ID No. 10], as for primer of glicoprotein E, 5'-gagatgcgaatatacgaat-3 [forward primer 4 (FP4); Seq. ID No. 11] and 5'-gtgggtgggctcggc-caaat-3' [reverse primer 4(RP4); Seq. ID No. 12], as for a primer of *Escherichia* cola of LacZ, 5'-gcgttacccaacttaatcg-3' [forward primer 5(FP5); Seq. ID No. 13] and 5'-tgtgagcgag-taacaacc-3' [reverse primer 5 (RP5); Seq. ID No. 14]; as for the primer for glyceraldehyde 3-phosphate dehydrogenase: GAPDH), 5'-cccatcaccatcttccagga-3' [forward primer 6 (FP6); Seq. ID No. 15] and 5'-ttgtcataccaggaaatggc-3' [reverse primer 6 (RP6); Seq. ID No. 16] were used to amplify DNA of 221 bp, 320 bp, 731 bp, respectively (J. Virol. 74, 3832-3841, 2000).

A-8 (Immunohistochemistry)

The specimens were fixed in Bouin's solution [15% (v/v) saturated picric acid solution, 1.65% (v/v) formalin, and 1% (v/v) acetic acid/PBS] and embedded in paraffin. Sections of 4 µm thickness were mounted on a poly-L-lysin coated microslides, treated in xylene, dehydrated through graded alcohol, and immersed in 70% methanol with $H_2O_2$ to block endogenous peroxidase. Then, antigen retrieval was performed using an autoclave at 121° C. for 10 minutes in a 10 mM citrate buffer (pH 7.0). The sections were incubated at room temperature for 1 hour using 1% (v/v) of goat serum/PBS, washed with PBS, and incubated with a polyclonal antibody against mouse calponin (*Genes to Cells* 3, 685-695, 1998), in 2% (w/v) BSA/PBS overnight at 4° C. The section mentioned above were washed 5 times with 0.005% (v/v) Tween 20/PBS, followed by incubation with biotinylated goat anti-rabbit IgG (TAGO Immunologicals) in 2% (w/v) BSA/PBS for 1 hour at room temperature, then incubated with avidinbiotin-horseradish peroxidase complex (Vector Laboratories) for 30 minutes at room temperature. After being washed in 0.005% (v/v) Tween 20/PBS, the final reaction product was washed with diaminobenzidine (WAKO Chemicals), and the sections were counterstained with hematoxyline for visualization. Tissue specimens treated with goat serum were used as a control to observe the non-specific stain.

A-9 (Statistical Analysis)

Statistical differences were determined using unpaired-Student's t-test. Differences were considered statistically significant with $p<0.05$.

EXAMPLE B

Results

B-1 (Identification of an Expression Regulatory Region of Human Calponin Promoter)

To identify the minimal promoter region which regulates the expression of human calponin, plasmids having various 5' deleted calponin promoter luciferase constructs were transfected into human osteosarcoma cell lines MNNG-HOS and HOS, and the mesangium cell line HMC. The Mesangium cell line HMC showed a stable growth pattern (hill and valley) characteristic of a smooth muscle-like phenotype and expressed smooth muscle-specific genes such as α-smooth muscle actin and SM22α. The calponin gene was most highly expressed in HMC among the three cell lines transfected (FIG. 1). As described previously (*Int. J. Cancer* 79, 245-250, 1998), calponin was expressed at the intermediate level in HOS, but was not expressed at all in MNNG-HOS (FIG. 1).

As a result of the transient transfection assay of plasmids p-288Luc and p-260Luc into HOS and HMC cells, luciferase activities for both increased by 4 times in HOS cell, 6 times in HMC cells than that of the assays when p-1159Luc was transfected. This shows that there is an expression regulatory region between −1159 to −288 of the calponin promoter region. There was a significant correlation between the expression of the calponin mRNA and the transcriptional activities of the promoter region from −385 and −260. As the bases were further deleted from −260 to −219, the promoter activity largely decreased in both HOS and HMC cells. Furthermore, when the constructs, where a large sections of the 5' region of the calponin gene promoter region are deleted (p-201Luc, p-176Luc and p-153Luc), were transfected, the luciferase activity was the same as when p-219Luc was used. These results indicate that the sequence between −260 to −219 is a positive expression regulatory region of calponin gene transcription in both HOS and HMC cells.

The region between −260 and −219 of the calponin gene promoter mentioned above, includes some sequence motifs similar to consensus binding sequences for Sox (AACAAT) at −258 and GATA-1 (CACAATCAGC; Seq. ID No. 17) at −250. When a part of the −260 to −239 region of the calponin gene promoter is deleted from p-260Luc, the transcriptional activity is decreased 50%. To test whether the putative binding site of Sox and GATA-1 and a region downstream of −239 show an expression regulatory function, 3 mutations were prepared by substituting −255/−254(AA to GG), −246/−244 (A to G at −246, C to T at −244), −232/−231 (CC to TT) of the plasmid p-260Luc, and the plasmids were transfected. In the transfection experiments in HMC cells, p-260 Luc activity for the 3 mutations mentioned above were 73±0.2%, 76±0.2%, 39±0.1%, respectively. These results suggest that all of the sequence encompassing −260 to −219 is required for the transcriptional activity of the calponin promoter.

B-2 (Regulation at the Transcriptional Level of the Expression of the Calponin Gene in Human Soft Tissue and Bone Tumor Cells)

To further assess whether there is a correlation between the expression of calponin and the transcriptional activity of the calponin promoter in human soft tissue and bone tumor cells, various human cell lines with or without calponin expression were transfected with p-260Luc or a construct containing the human 4F2 heavy-chain transcriptional enhancer (*Mol. Cell. Biol.* 9, 2588-2597, 1987) inserted upstream of p-260Luc (p4F2-260Luc). By RT-PCR analysis, the expression of calponin mRNA was observed in synovial sarcoma cells and SK-LMS-1 leimyosarcoma cells. By contrast, the expression of calponin in OST osteosarcoma cells was very low (FIG. 2). As it is shown in FIG. 2, in all the cells examined, the transcriptional activities of p-260 Luc and p4F2-260Luc were correlated with the expression level of transcripts of calponin mRNA. These experimental results indicate that the expression of the calponin gene in human soft tissue and bone tumor cells may be regulated at the transcriptional level by a 260-bp sequence upstream of the translation initiation site. Moreover, the 4F2 enhancer inserted upstream of the calponin promoter, and the transcriptional activity of p-260Luc in calponin-positive synovial sarcoma and SK-LMS-1 cells increased from 3 to 5 times. Therefore, in the following experiment, the 4F2 enhancer/−260 calponin promoter sequence was used to regulate expression of the HSV ICP4 gene in human soft tissue and bone tumor cells.

B-3 (Selective Replication of a Recombinant Hsv Vector in Calponin-Positive Cells In Vitro)

To construct an HSV vector that replicates selectively in calponin-positive cells and proliferating cells, a DNA fragment containing the 4F2 enhancer/−260 calponin promoter/ICP4 (pTKΔ-CALP-ICP4) was inserted into the TK locus (U$_L$23) of ICP4—HSV mutant d120 (*J. Virol.* 56, 558-570, 1985) to prepare d12.CALP. The plasmid pTKΔ-CALF-ICP4 contains 2 chimeric transgenes expressing ICP4 protein and β-glactosidase where *Escherichia coli*-derived LacZ was inserted (FIG. 3A). Human cell lines with or without calponin expression were used to assess the selectivity of d12.CALP viral replication (FIG. 3B).

The cell lines constructed as mentioned above were infected with d.12CALP or hrR3 at the multiplicity of infection of 0.001 for 48 hours. Plaque formation was assessed to evaluate viral replication (FIG. 3C). In calponin-positive synovial sarcoma cells, SK-LMS-1 cells and HOS cells, d12.CALP showed similar cytopathic effects as that of hrR3. In contrast, in calponin-negative SKN cells, OST cells, MNNG-HOS cells and HUVEC cells, no apparent cell lysis by d12.CALP was observed. Desmoid cells, which showed the slowest proliferation speed, expressed mRNA of calponin at a same level as SK-LMS-1 cells, but no apparent formation of plaque by d12.CALP was observed. These results show that the cytopathic effect by d12.CALP depends on both the expression of calponin and the cell proliferation speed.

As it can be seen from FIGS. 4A and 4B, when d12.CALP is infected in SK-LMS-1 cells and synovial sarcoma cells at low multiplicity of infection (MOI:0.001), a complete ontolysis of the cultures in a 10 cm-dish was observed 96 hours after infection. It was also confirmed that the cytolysis of synovial sarcoma cells spread from cell to cell (FIG. 4A). Among the SK-LMS-1 infected cells, some were multi-nucleated before lysis (FIG. 4B, arrow).

Figure 5:
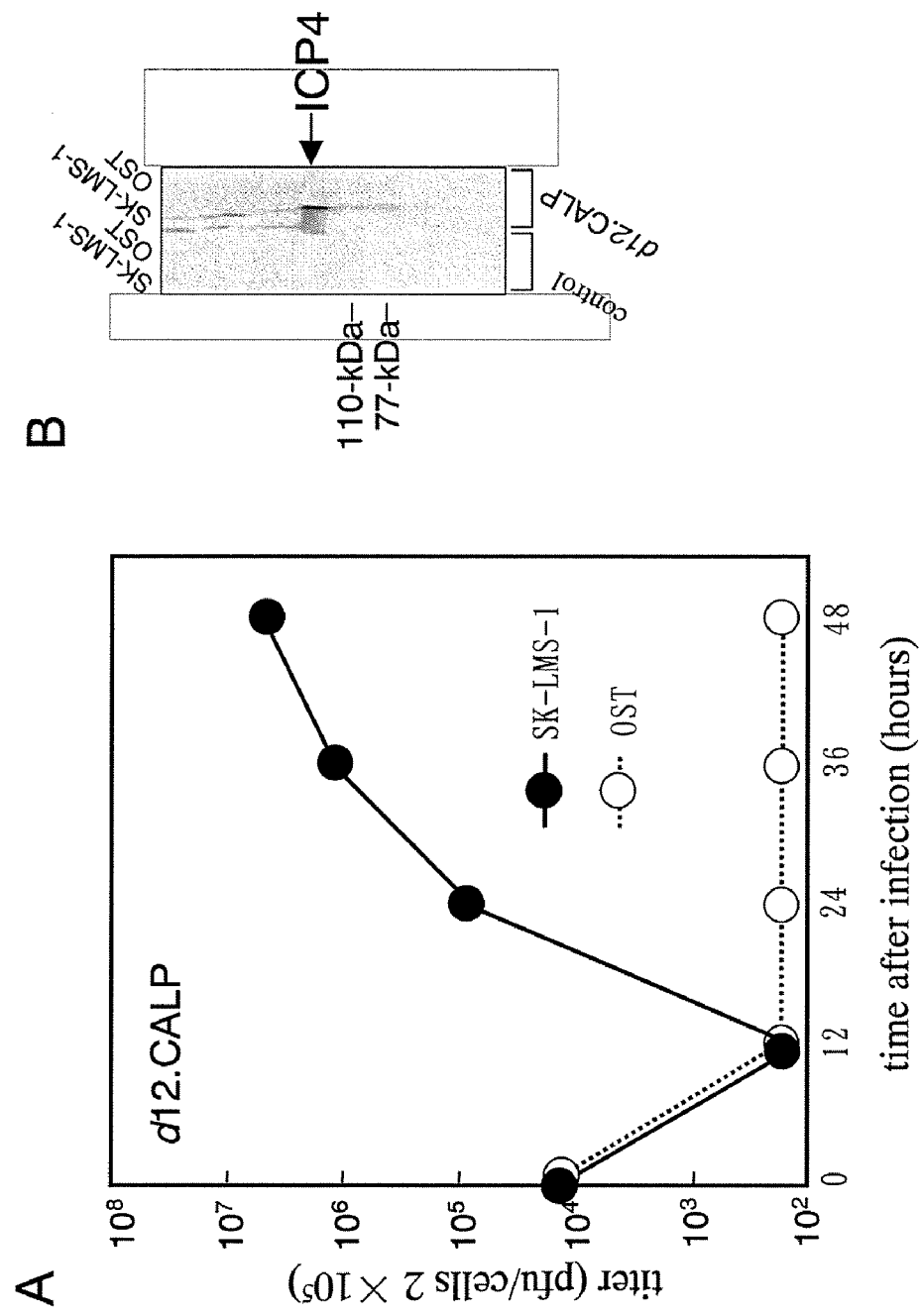
FIG. 5 shows the selective injury activity of d12.CALP in calponin-positive cells in vitro.

Viral titers were assessed by single step growth assays.

d12.CALP replicated in calponin-positive SK-LMS-1 cells but the titers of d12.CALP decreased in calponin-negative OST cells 48 hours after infection from $1/10^6$ to $1/10^7$ compared to SK-LMS-1 cells (FIG. 5A). By conducting immunoblot analysis of cell extracts 22 hours after infection, it was found that ICP4 protein was expressed in SK-LMS-1 cells but that ICP4 protein was not expressed in OST cells. This was consistent with the result of viral replication assay (FIG. 5B). In contrast, the d120 viral vector did not show generation of viral progenies at all in cultures of SK-LMS-1 and OST.

B-4 (Treatment of Human Leiomyosarcoma Xenografts with a Recombinant HSV Vector)

Figure 6:
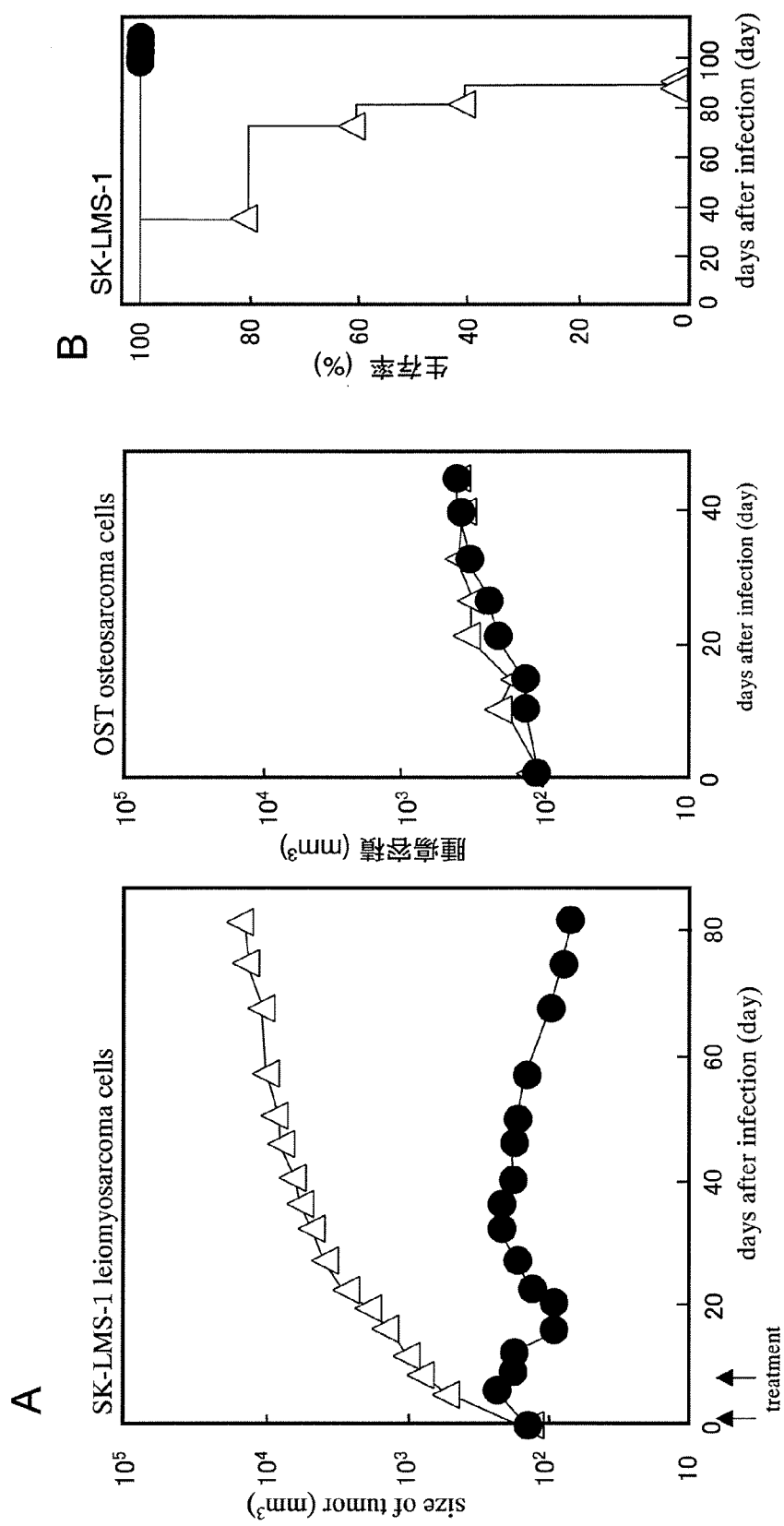
FIG. 6 shows the suppressing effect of tumor formation of d12.CALP in vivo.
Figure 7:
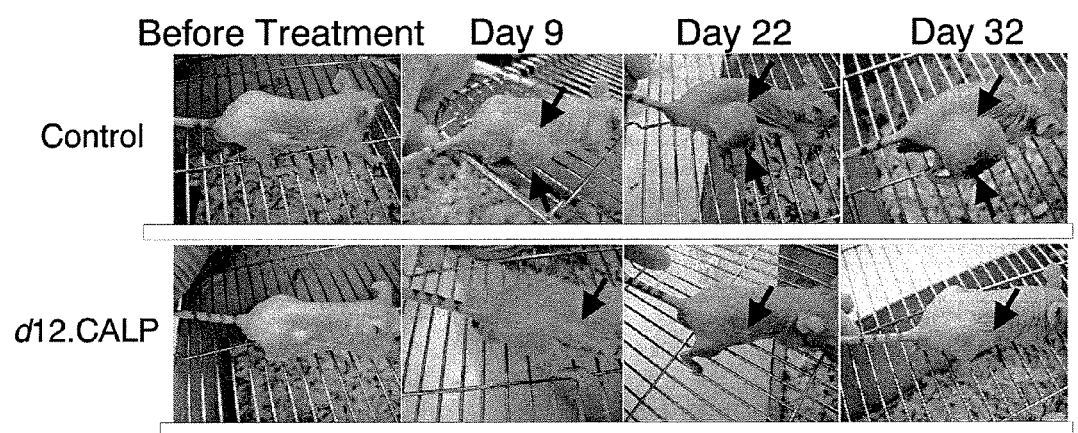
FIG. 7 shows nude mice treated with d12.CALP.

To evaluate the effect of d12.CALP in a treatment in vivo, SK-LMS-1 leiomyosarcoma xenografts were settled to nude mice, and $1\times10^7$ pfu d12.CALP per tumor volume of 100 mm$^3$ was administered twice. As a control, the virus buffer alone was administered to the tumor sites. Before the treatment, there was no significant difference between the tumors treated with d12.CALP and the control tumors, in tumor volume (138±20 and 139±28 mm$^3$, respectively, n=5), or in the expression levels of immuno-reactive calponin. The infection of d12.CALP showed an association with the growth suppression of SK-LMS-1 tumors, but there was no association with growth suppression of calponin-negative OST tumors (FIG. 6A). On the contrary, in the treatment of SK-LMS-1 xenografts with a virus buffer alone, the growth of progressive tumors and the death of all the animals (n=5) were confirmed by 89 days after the treatment, and it was found that it was associated with the progressive tumor growth and death of animals (FIG. 6B). By 5 weeks after the initial d12.CALP infection, it was confirmed that the tumors were completely regressed in 4 out of 5 mice (FIG. 7). In one mouse, the tumor was regrown. Therefore, the recurrent tumor of this mouse was treated again with d12.CALP, and the tumor growth was suppressed in a stable manner.

Figure 8:
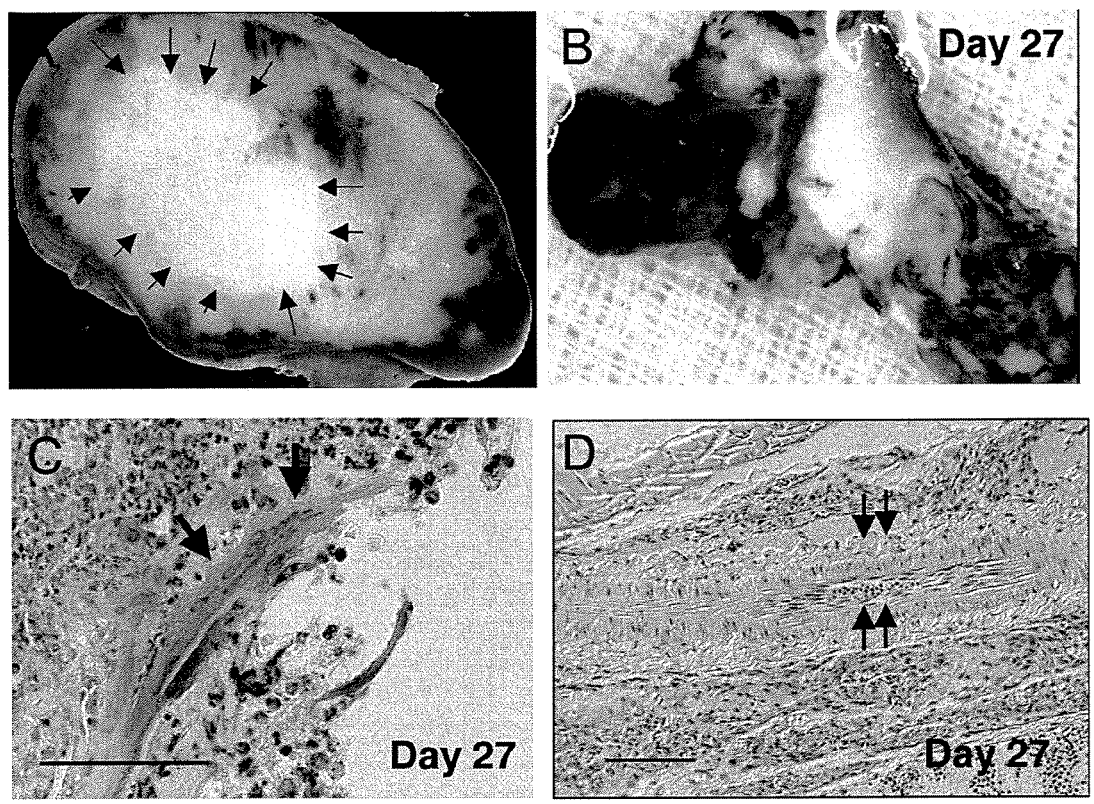
FIG. 8 is a picture that shows replication of d12.CALP in vivo.

In histochemical staining with X-gal, the expression of β-galactosidase was observed by introducing LacZ to the TK locus in SK-LMS-1 tumor cells treated with d12.CALP (FIGS. 8A and 8B), but was not observed in control tumor cells. By this result, the region where d12.CALP viruses spread in vivo was identified. At day 8, necrosis began to be noticeable, and the expression of LacZ was lacking in this region (FIG. 8A, arrow). At a higher magnification, as observed in cytophathic assays in vitro, it was found that some of the cells among the tumor cells stained blue were multi-nucleated (FIG. 8C, arrow), and these were losing their typical morphological appearance of SK-LMS-1 cells. However, as it is shown in FIG. 8D, the expression of LacZ was negative for smooth muscle cells surrounding normal blood vessels in virus-infected mice. Furthermore, by PCR analysis, LacZ sequence specific to d12.CALP could not be confirmed in DNA prepared from brain, lung, liver, kidney, heart, small intestine or uterus prepared 8 days after administration of d12.CALP into the tumors (FIG. 8E). In organs including aortic or gastrointestinal smooth muscles, viral replication and expression of LacZ were not observed histologically.

B-5 (Spread of Recombinant HSV Vector in Tumor)

In order to assess whether d12.CALP, which was injected into SK-LMS-1 xenografts and replicated, could target tumor cells which are located in a distant place via the blood vessels, d12.CALP was inoculated in tumors in SK-LMS-1 xenograft in the right flank, and the virus distribution at SK-LMS-1 xenograft in the left flank was examined. As it is of FIG. 9A, the expression of β-glactosidase in tumor cells in the left flank was confirmed at day 20, as well as in the site of inoculation. Histologically, tumor necrosis was observed in a wide range, in both tumors at the right flank and tumors at the left flank but as it is of FIG. 9B, no effect by d12.CALP was observed in calponin-positive smooth muscle cells surrounding normal blood vessels.

Figure 9:
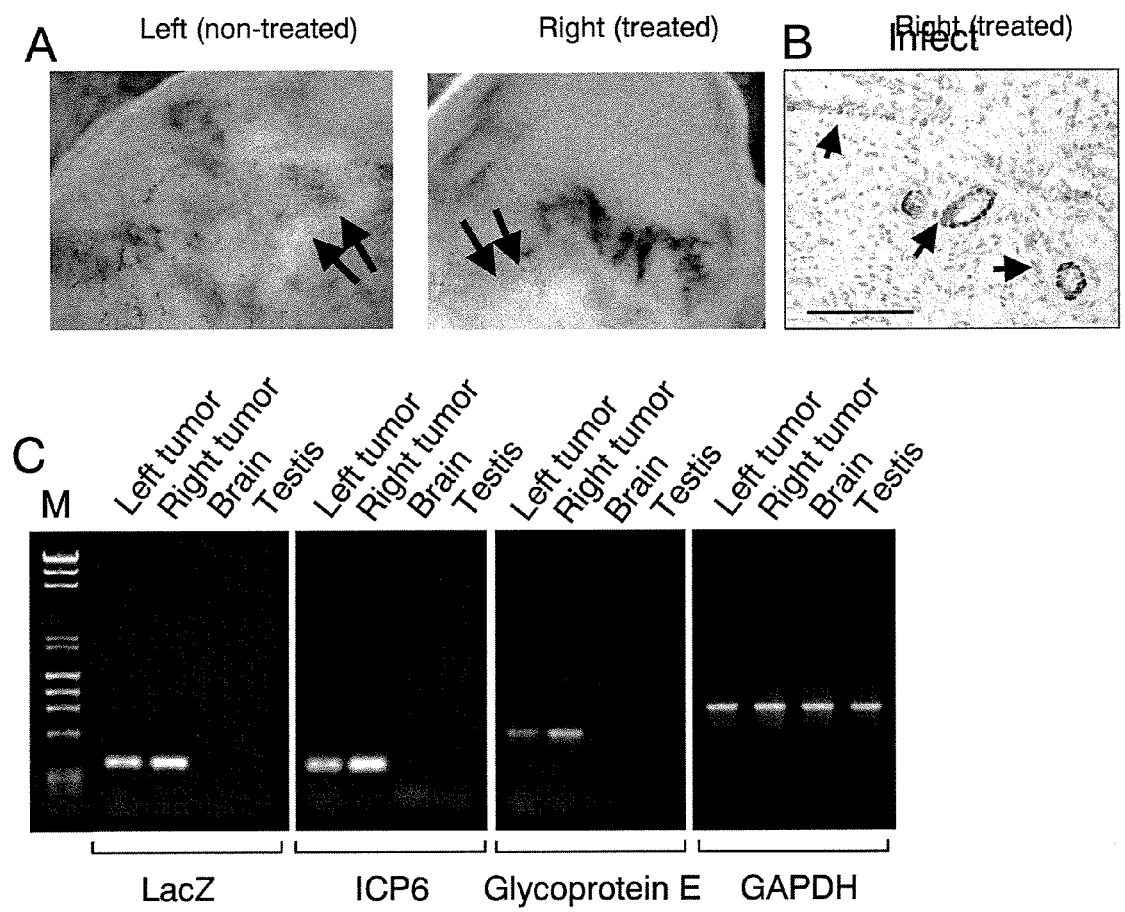
FIG. 9 shows that d12.CALP diffuses and replicates at a site distant from the infection site in vivo.

By performing PCR analysis using primers to ribonucleotide reductase(ICP6), glycoprotein E or *Escherichia coli*-derived LacZ, which were inserted in the TK locus, it was found that virus DNA derived from d12.CALP spread in tumor tissues in both flanks but did not spread in tumor tissues in brain or testes (FIG. 9C).

B-6 (Selective Injury Activity to Tumor Neovascular Smooth Muscle Cells)

Figure 10:
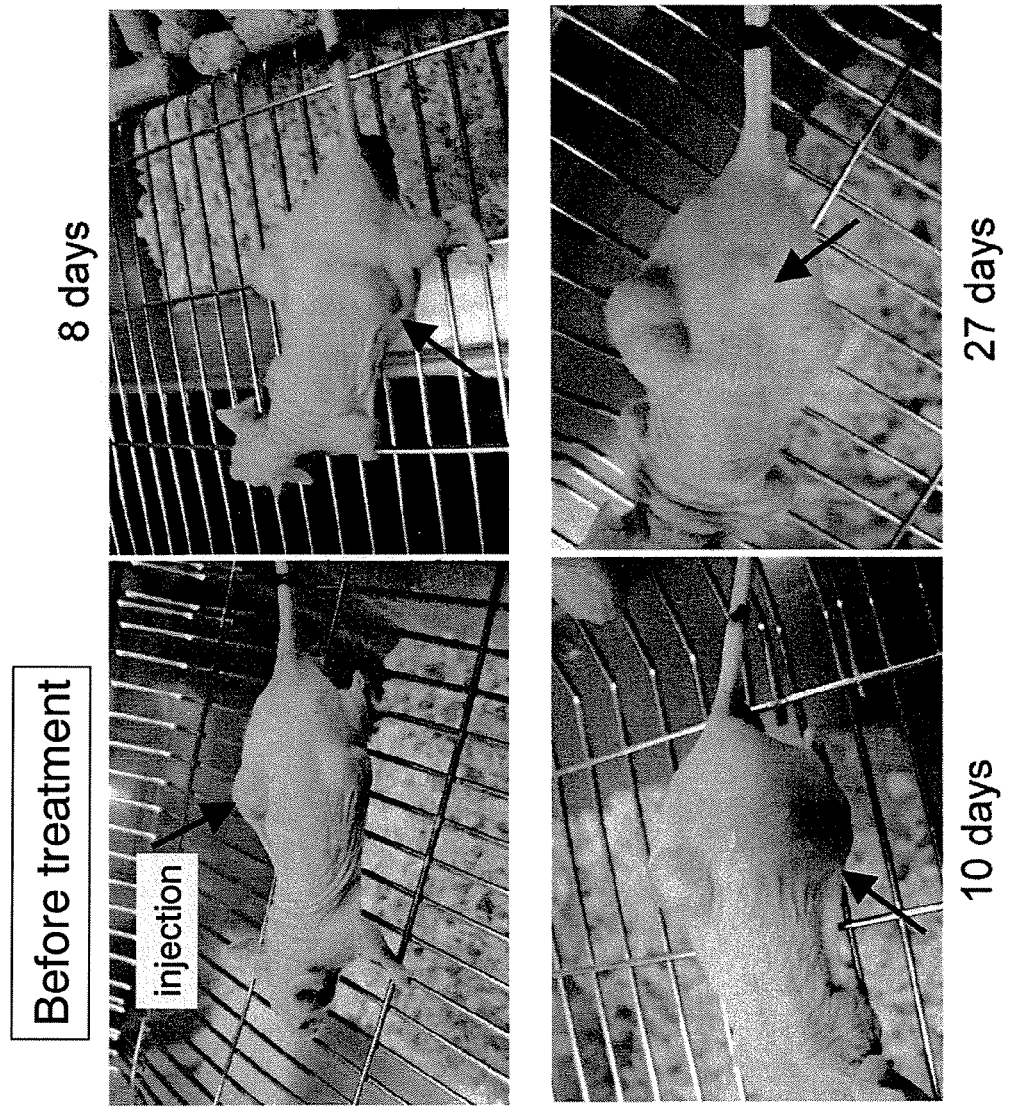
FIG. 10 shows an explosion of a tumor vessel by a selective injury activity toward tumor neovascular smooth muscle cells of d12.CALP in vivo; and the reduction of the tumor due to hemorrhagic necrosis of the tumor cells.

Human leiomyosarcoma cells were xenotransplanted beneath the skin of both dorsal parts of a nude mouse, and d12.CALP was injected into one side (right side). At day 8 after injection, bleeding occurred in the xenograft at the opposite side (left side), and the tumors diminished (n=4) (FIG. 10). As for the leiomyosarcoma used in this experiment, it was confirmed that d12.CALP does not injure the tumor cells itself. In an infection experiment in vitro, the retraction of the tumors was thought to be the result of the fact that d12.CALP has hematogenously reached the tumor at the opposite side and has injured the tumor blood vessels. Actually, by investigating the histology of the tumors 2 days after bleeding, an image of wide hemorrahagic necrosis of the tumor cells and disruption of the blood vessels were observed. Moreover, by immunohistochemical analysis, the expression of LacZ and ICP 4 protein was observed in the cells surrounding blood vessels. On the other hand, in the smooth muscle cells of normal blood vessels contacting the tumors, cell injury was not observed.

INDUSTRIAL APPLICABILITY

A malignant tumor derived from mesenchymal cells, that is a sarcoma, is resistant to chemotherapy or radiotherapy and continues to relapse even after surgical resection, and by eventually spreading to lung, liver, peritonuem and the like, leads to patient death. The number of cases in Japan is up to 5000 to 10000 annually, including mainly sarcoma in the bone and soft tissue in the field of orthopedic surgery, and including leimyosarcoma in the field of gynecological, stroma sarcoma in the field of digestive surgery, malignant mesothelioma in the field of chest/digestive surgery, fibrosarcoma, malignant meninagiomo, neurilemmmoma in the field of neurosurgery and the like. Although it represents only about 1% of carcinoma, it generates frequently affecting young people. Furthermore, there is no effective treatment, and the development of a new treatment method is strongly required socially. Embodiments of the present invention address such requirements, and provide a cell-specific replication-competent vector, which does not target normal cells, which expresses specifically in particular cells such as malignant tumor cells and the like, and using the cell-specific replication-competent vector, the first gene therapy in the world being selective for sarcoma cells can be possible. Especially, as the calponin gene is expressed in 31% of gastrointestinal stromal tumor (GIST), 91% of leiomyosarcoma, 38% of stroma tumor in the field of digestive surgery, 60% of osteosarcoma, and 32% of soft part sarcoma other than leiomyosarcoma, the therapeutic drug of the present invention can be used as an effective treatment of cancer to all solid cancers and among them, can be used effectively in a new gene therapy that selectively disrupts tumor vessels.

The invention claimed is:

1. An isolated DNA consisting of the nucleotide sequence of Seq. ID No. 1 or the complementary sequence thereof.

2. An isolated DNA consisting of the nucleotide sequence of Seq. ID No. 2 or the complementary sequence thereof.

3. An isolated DNA consisting of the nucleotide sequence of Seq. ID No. 3 or the complementary sequence thereof.

4. An isolated DNA comprising a nucleotide sequence consisting of a truncated calponin promoter set forth by SEQ ID NO: 1 or 2 and an heterologous enhancer operably linked upstream of the truncated calponin promoter, wherein the isolated DNA does not comprise the full-length calponin promoter.

5. The isolated DNA according to claim 4, wherein the enhancer is a 4F2 enhancer.